United States Patent
Lin

(10) Patent No.: US 10,190,146 B2
(45) Date of Patent: *Jan. 29, 2019

(54) METHOD OF CORRECTING FOR OXYGEN EFFECT

(71) Applicant: Ascensia Diabetes Care Holdings AG, Basel (CH)

(72) Inventor: Jing Lin, Belmont, MA (US)

(73) Assignee: Ascensia Diabetes Care Holdings AG, Basel (CH)

(*) Notice: Subject to any disclaimer, the term of this patent is extended or adjusted under 35 U.S.C. 154(b) by 129 days.

This patent is subject to a terminal disclaimer.

(21) Appl. No.: 15/370,033

(22) Filed: Dec. 6, 2016

(65) Prior Publication Data

US 2017/0081694 A1 Mar. 23, 2017

Related U.S. Application Data

(60) Continuation of application No. 13/302,325, filed on Nov. 22, 2011, now Pat. No. 9,534,244, which is a division of application No. 12/225,785, filed as application No. PCT/US2007/008386 on Apr. 5, 2007, now abandoned.

(Continued)

(51) Int. Cl.
*C12Q 1/00* (2006.01)
*G01N 27/327* (2006.01)

(52) U.S. Cl.
CPC .............. *C12Q 1/006* (2013.01); *C12Q 1/004* (2013.01); *G01N 27/3274* (2013.01)

(58) Field of Classification Search
CPC ..... C12Q 1/006; C12Q 1/004; G01N 27/3274
See application file for complete search history.

(56) References Cited

U.S. PATENT DOCUMENTS 4,431,004 A 2/1984 Bessman et al.
5,660,791 A 8/1997 Brenneman et al.
(Continued)

FOREIGN PATENT DOCUMENTS

EP 0 245 073 A2 5/1987 ............. G01N 27/46
EP 1 734 362 A2 12/2006 ........... G01N 33/478
(Continued)

OTHER PUBLICATIONS

Cassidy, J.F., Clinton, C., Breen, W., Foster, R., O'Donoghur, E., Analyst 118 (1993) 415-418. Novel Electrochemical Device for the Detection of Cholesterol or Glucose.
(Continued)

*Primary Examiner* — Louis J Rufo
(74) *Attorney, Agent, or Firm* — Nixon Peabody LLP

(57) ABSTRACT

An electrochemical test sensor is adapted to measure glucose and correct for the oxygen effect in a fluid sample. The test sensor comprises a base, first and second working electrodes, and a counter electrode. The first working electrode includes glucose oxidase, a mediator and peroxidase. The second working electrode includes glucose oxidase and the mediator. The first working electrode, the second working electrode and the counter electrode are located on the base. In other embodiments, an electrochemical test sensor is adapted to measure cholesterol, lactate, pyruvate or xanthine and correct for the oxygen effect in a fluid sample.

21 Claims, 7 Drawing Sheets

Related U.S. Application Data

(60) Provisional application No. 60/838,619, filed on Aug. 18, 2006, provisional application No. 60/790,607, filed on Apr. 10, 2006.

(56) References Cited

U.S. PATENT DOCUMENTS

| | | | |
|---|---|---|---|
| 5,755,953 | A | 5/1998 | Henning et al. |
| 5,759,364 | A | 6/1998 | Charlton et al. |
| 5,798,031 | A | 8/1998 | Charlton et al. |
| 6,531,040 | B2 | 3/2003 | Musho et al. |
| 6,767,440 | B1 | 7/2004 | Bhullar et al. |
| 6,767,441 | B1 * | 7/2004 | Cai ............ C12Q 1/004 204/403.03 |
| 6,841,052 | B2 | 1/2005 | Musho et al. |
| 9,534,244 | B2 * | 1/2017 | Lin ............. C12Q 1/004 |
| 9,546,390 | B2 * | 1/2017 | Lin ............. C12Q 1/004 |
| 2001/0042683 | A1 | 11/2001 | Musho et al. |
| 2002/0185375 | A1 | 12/2002 | Wogoman |
| 2003/0032190 | A1 | 2/2003 | Brown et al. |
| 2004/0007461 | A1 | 1/2004 | Edelbrock et al. |
| 2004/0200720 | A1 | 10/2004 | Musho et al. |
| 2004/0245121 | A1 | 12/2004 | Nagakawa et al. |
| 2004/0253367 | A1 | 12/2004 | Wogoman |
| 2006/0278537 | A1 * | 12/2006 | Cai ............... A61B 5/14546 205/777.5 |

FOREIGN PATENT DOCUMENTS

| | | | | |
|---|---|---|---|---|
| WO | WO 00/73785 | A2 | 12/2000 | ............ G01N 33/00 |
| WO | WO 01/0100865 | A2 | 1/2001 | ............... C12Q 1/00 |
| WO | WO-0100865 | A2 * | 1/2001 | ............ C01B 15/01 |
| WO | WO 03/012422 | A1 | 2/2003 | .......... G01N 27/327 |
| WO | WO 03/097866 | A1 | 11/2003 | ............... C12Q 1/26 |
| WO | WO 07/008386 | A2 | 1/2007 | ............ G06F 17/30 |

OTHER PUBLICATIONS

Chaubey, A., Malhotra, Bid., Biosensors & Bioelectronics 17 (2002) 441-456. Medicated Biosensors.

Wilson, R., Turner, A.P.F., Biosensors & Bioelectronics 7 (1992) 165.

Written Opinion corresponding to International Patent Application No. PCT/US2007/008386, European Patent Office, dated Oct. 15, 2007, 6 pages.

International Search Report corresponding to International Patent Application No. PCT/US2007/006098, European Patent Office, dated Oct. 15, 2007, 4 pages.

* cited by examiner

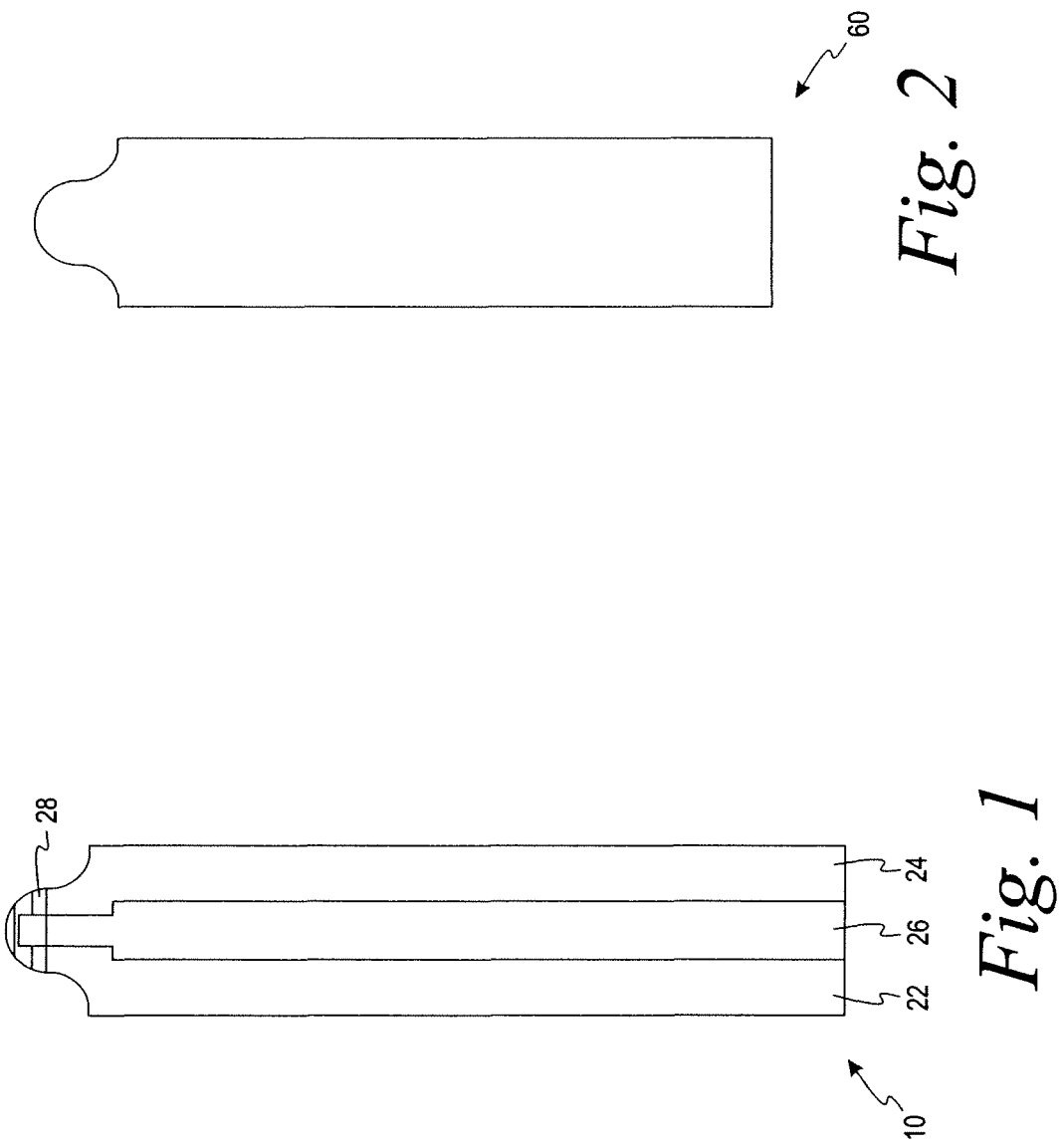

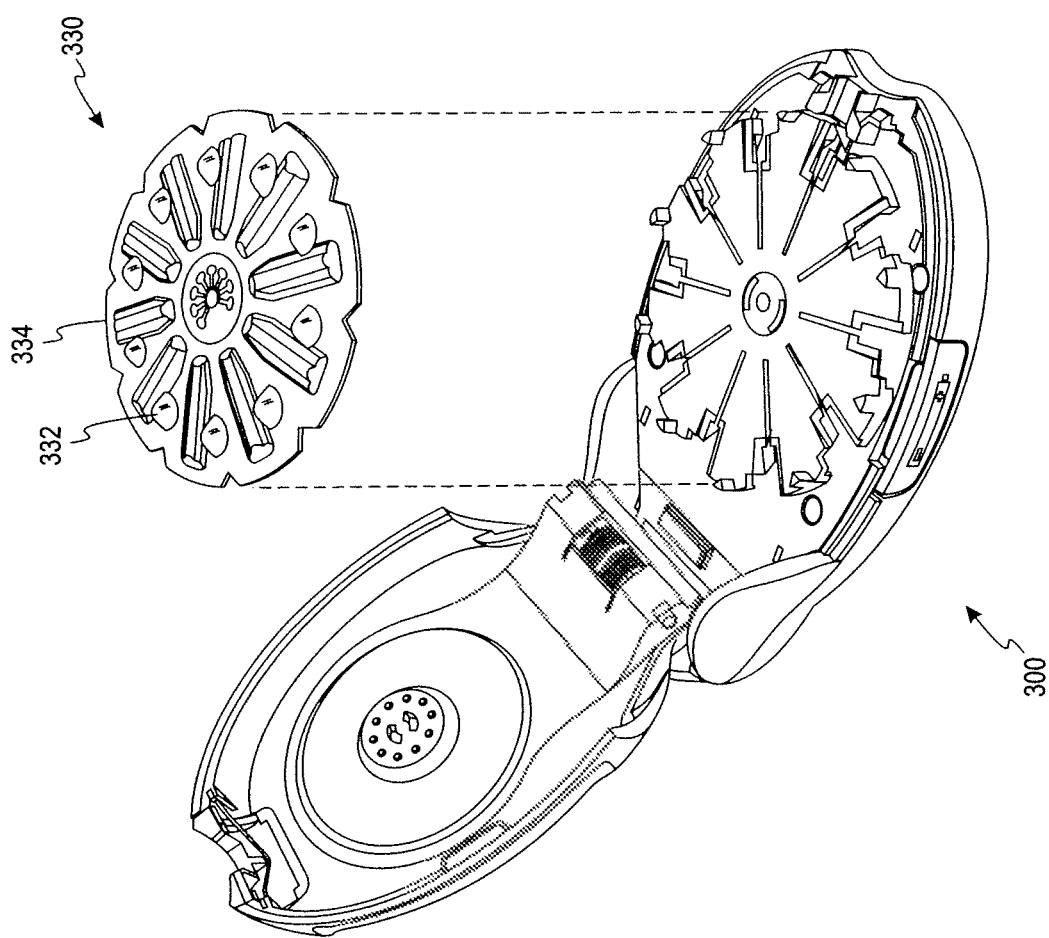

METHOD OF CORRECTING FOR OXYGEN EFFECT

CROSS-REFERENCE TO RELATED APPLICATIONS

This application is a continuation of application Ser. No. 13/302,325 filed on Nov. 22, 2011, which has been allowed; application Ser. No. 13/302,325 filed on Nov. 22, 2011 is a divisional of application Ser. No. 12/225,785 filed on Sep. 29, 2008 and which is now abandoned; application Ser. No. 12/225,785 is the national phase of Application No. PCT/US2007/008386 filed Apr. 5, 2007, which claims priority back to Provisional Application Nos. 60/790,607 filed on Apr. 10, 2006 and 60/838,619 filed on Aug. 18, 2006, all of which are incorporated by reference in their entireties.

FIELD OF THE INVENTION

The present invention relates generally to a test sensor that corrects for the oxygen effect and a method of using the same. More specifically, the present invention relates to a test sensor using reagents (e.g., glucose oxidase) that assists in determining the analyte concentration (e.g., glucose concentration) in a fluid and corrects for the oxygen effect.

BACKGROUND OF THE INVENTION

The quantitative determination of analytes in body fluids is of great importance in the diagnoses and maintenance of certain physiological abnormalities. In particular, it is important that diabetic individuals frequently check the glucose level in their body fluids to regulate the glucose intake in their diets. The results of such tests can be used to determine what, if any, insulin or other medication needs to be administered. In one type of blood-glucose testing system, test sensors are used to test a sample of blood.

A test sensor contains biosensing or reagent material that reacts with blood glucose. The testing end of the test sensor is adapted to be placed into the fluid being tested, for example, blood that has accumulated on a person's finger after the finger has been pricked. The fluid is drawn into a capillary channel that extends in the test sensor from the testing end to the reagent material by capillary action so that a sufficient amount of fluid to be tested is drawn into the test sensor. Alternatively, the person could apply a drop of blood to the test sensor that contains biosensing or reagent material that reacts with blood glucose.

Two reagents that are commonly used to determine glucose concentration are glucose dehydrogenase (GDH) and glucose oxidase (GO). Types of glucose dehydrogenase that may be used are pyrroloquinoline quinone glucose dehydrogenase (PQQ-GDH) and NAD-dependent glutamate dehydrogenase (NAD-GDH). PQQ-GDH is generally a stable reagent, but one disadvantage of PQQ-GDH is its cross-reactivity with maltose, which may be problematic with certain individuals. NAD-GDH tends to be less stable than PQQ-GDH and currently is more costly than either glucose oxidase or PQQ-GDH.

Glucose oxidase is currently not an expensive reagent, especially compared to NAD-GDH. In addition, glucose oxidase is generally a stable reagent and typically is more stable than PQQ-GDH and NAD-GDH. One disadvantage of using a glucose oxidase in a test sensor, however, is its sensitivity to the oxygen level in, for example, a blood sample to be tested. In determining the glucose concentration using glucose oxidase in a blood sample, the oxygen effect may sometimes be as great as 20%.

It would be desirable to use a test sensor with glucose oxidase that corrects for the oxygen effect and, thus, results in making more accurate glucose measurements. It would also be desirable to use a test sensor with other reagents that corrects for the oxygen effect and, thus, results in more accurate analyte measurements.

SUMMARY OF THE INVENTION

According to one embodiment, an electrochemical test sensor is adapted to measure glucose and correct for the oxygen effect in a fluid sample. The test sensor comprises a base, first and second working electrodes, and a counter electrode. The first working electrode includes glucose oxidase, a mediator and peroxidase. The second working electrode includes glucose oxidase and the mediator. The first working electrode, the second working electrode and the counter electrode are located on the base.

According to another embodiment, an electrochemical test sensor is adapted to measure glucose and correct for the oxygen effect in a fluid sample. The test sensor comprises a base, first and second working electrodes, a counter electrode and a lid. The first working electrode includes glucose oxidase, a mediator and peroxidase. The second working electrode includes glucose oxidase and the mediator. The lid is attached to the base. The first working electrode, the second working electrode and the counter electrode are located on either the base or the lid.

According to another embodiment, an electrochemical test sensor is adapted to measure glucose and correct for the oxygen effect in a fluid sample. The test sensor comprises a base, first and second working electrodes, a counter electrode, a lid and a spacer. The first working electrode includes glucose oxidase, a mediator and peroxidase. The second working electrode includes glucose oxidase and the mediator. The spacer is located between the lid and the base. The first working electrode, second working electrode and the counter electrode are located adjacent to the base.

According to one method, the oxygen effect in determining the concentration of glucose using an electrochemical test sensor is corrected. A test sensor is provided and comprises a base, first and second working electrodes, and a counter electrode. The first working electrode includes glucose oxidase, a mediator and peroxidase. The second working electrode includes glucose oxidase and the mediator. The first working electrode, the second working electrode and the counter electrode is adjacent to the base. The test sensor contacts a meter to form an electrical connection. Fluid is placed on the test sensor. A first current from the first working electrode is measured. A second current from the second working electrode is measured. The concentration of glucose is determined using the first current measurement and the second current measurement.

According to another embodiment, an electrochemical test sensor is adapted to measure cholesterol and correct for the oxygen effect in a fluid sample. The test sensor comprises a base, first working electrode, second working electrode and a counter electrode. The first working electrode includes cholesterol oxidase, a mediator and peroxidase. The second working electrode includes cholesterol oxidase and the mediator. The first working electrode, the second working electrode and the counter electrode are located on the base.

According to a further embodiment, an electrochemical test sensor is adapted to measure cholesterol and correct for the oxygen effect in a fluid sample. The test sensor comprises a base, first working electrode, second working electrode, a counter electrode and a lid. The first working electrode includes cholesterol oxidase, a mediator and peroxidase. The second working electrode includes cholesterol oxidase and the mediator. The lid is attached to the base. The first working electrode, the second working electrode and the counter electrode are located on either the base or the lid.

According to yet another embodiment, an electrochemical test sensor is adapted to measure cholesterol and correct for the oxygen effect in a fluid sample. The test sensor comprises a base, first working electrode, second working electrode, a counter electrode, a lid and a spacer. The first working electrode includes cholesterol oxidase, a mediator and peroxidase. The second working electrode includes cholesterol oxidase and the mediator. The spacer is located between the lid and the base. The first working electrode, the second working electrode and the counter electrode are located adjacent to the base.

According to another method, the oxygen effect is corrected in determining the concentration of cholesterol using an electrochemical test sensor. A test sensor is provided and comprises a base, first and second working electrodes, and a counter electrode. The first working electrode includes cholesterol oxidase, a mediator and peroxidase. The second working electrode includes cholesterol oxidase and the mediator. The first working electrode, the second working electrode and the counter electrode are adjacent to the base. The test sensor contacts a meter to form an electrical connection. A fluid is placed on the test sensor. A first current is measured from the first working electrode. A second current is measured from the second working electrode. The concentration of cholesterol is determined using the first current measurement and the second current measurement.

According to one embodiment, an electrochemical test sensor is adapted to measure at least one of lactate, pyruvate or xanthine and correct for the oxygen effect in a fluid sample. The test sensor comprises a base, first working electrode, second working electrode and a counter electrode. The first working electrode includes lactate, pyruvate or xanthine oxidase, a mediator and peroxidase. The second working electrode includes lactate, pyruvate or xanthine oxidase and the mediator. The first working electrode, the second working electrode and the counter electrode are located on the base.

According to another embodiment, an electrochemical test sensor is adapted to measure at least one of lactate, pyruvate or xanthine and correct for the oxygen effect in a fluid sample. The test sensor comprises a base, first working electrode, second working electrode, a counter electrode and a lid. The first working electrode includes lactate, pyruvate or xanthine oxidase, a mediator and peroxidase. The second working electrode includes lactate, pyruvate or xanthine oxidase and the mediator. The lid is attached to the base. The first working electrode, the second working electrode and the counter electrode are located on either the base or the lid.

According to a further embodiment, an electrochemical test sensor is adapted to measure at least one of lactate, pyruvate or xanthine and correct for the oxygen effect in a fluid sample. The test sensor comprises a base, first working electrode, second working electrode, a counter electrode, a lid and a spacer. The first working electrode includes lactate, pyruvate or xanthine oxidase, a mediator and peroxidase. The second working electrode includes lactate, pyruvate or xanthine oxidase and the mediator. The spacer is located between the lid and the base. The first working electrode, the second working electrode and the counter electrode are located adjacent to the base.

According to another method, the oxygen effect is corrected in determining the concentration of at least one of lactate, pyruvate or xanthine using an electrochemical test sensor. A test sensor is provided and comprises a base, first and second working electrodes, and a counter electrode. The first working electrode includes lactate, pyruvate or xanthine oxidase, a mediator and peroxidase. The second working electrode includes lactate, pyruvate or xanthine oxidase and the mediator. The first working electrode, the second working electrode and the counter electrode are adjacent to the base. The test sensor contacts a meter to form an electrical connection. A fluid is placed on the test sensor. A first current is measured from the first working electrode. A second current is measured from the second working electrode. The concentration of lactate, pyruvate or xanthine is determined using the first current measurement and the second current measurement.

BRIEF DESCRIPTION OF THE DRAWINGS

FIG. 1 is a top view of a base to be used in forming a test sensor according to one embodiment.

FIG. 2 is a top view of a lid to be used in forming a test sensor according to one embodiment.

FIG. 3b is a side view of the test sensor of FIG. 3a.

FIG. 4b is an enlarged view of the generally circular region FIG. 4b in FIG. 4a.

FIG. 5 is a perspective view of a sensor-dispensing instrument or meter in the open position showing a sensor pack being inserted according to one embodiment.

FIG. 6b is a front view of a sensor-dispensing instrument according to one embodiment that is adapted to receive the cartridge of FIG. 6a.

DESCRIPTION OF ILLUSTRATED EMBODIMENTS

The present invention in one embodiment is directed to an electrochemical test sensor comprising glucose oxidase that is adapted to test a fluid and to correct for the oxygen effect, especially in a blood sample. By reducing the effect of oxygen, the glucose measurements are improved. The analytes may be in, for example, a whole blood sample, a blood serum sample, a blood plasma sample, other body fluids such as ISF (interstitial fluid), urine, and non-body fluids. As used within this application, the term "concentration" refers to an analyte concentration, activity (e.g., enzymes and electrolytes), titers (e.g., antibodies), or any other measure of concentration used to measure the desired analyte. The test sensor to be used in the present invention is an electrochemically-based test sensor.

The electrochemical test sensors typically include at least a base and a lid. The base and lid may be made from a variety of materials such as polymeric materials. Non-limiting examples of polymeric materials that may be used to form the base and lid include polycarbonate, polyethylene terephthalate (PET), polyethylene naphthalate (PEN), polyimide and combinations thereof. As will be discussed below, the test sensors may include an additional layer such as a spacer. Thus, in one embodiment, the electrochemical test sensor includes a base, spacer and lid.

The electrochemical test sensors to be used in determining the glucose concentration are typically provided with a capillary channel that extends from the front or testing end of the test sensors to the biosensing or reagent material disposed in the test sensor. The reagent may be stored within the test sensor in a dried ink form to promote an extended shelf life of the test sensor. When the testing end of the test sensor is placed into fluid (e.g., blood that is accumulated on a person's finger after the finger has been pricked), a portion of the fluid is drawn into the capillary channel by capillary action. The fluid then mixes with the reagent material in the test sensor and chemically reacts with the reagent material so that an electrical signal indicative of the glucose level in the fluid being tested is supplied and subsequently transmitted to a sensor-dispensing instrument or meter.

Figure 3A:
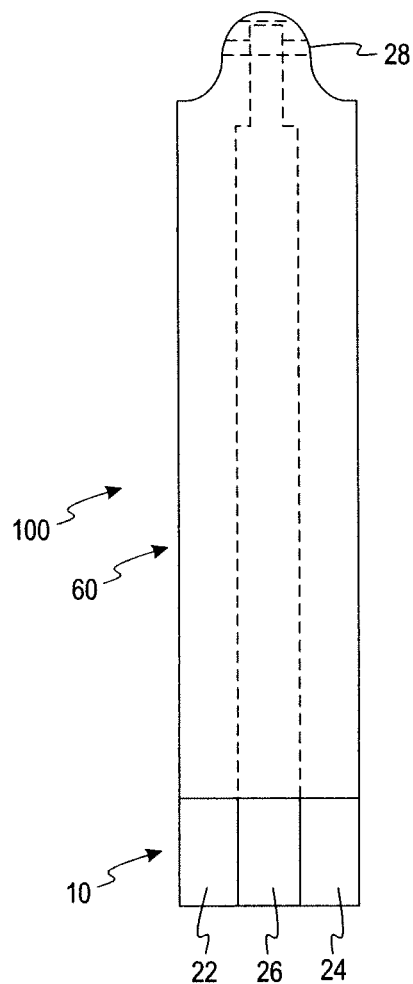
FIG. 3a is a top view of the test sensor using the base of FIG. 1, the lid of FIG. 2 and an adhesive according to one embodiment.
Figure 3B:
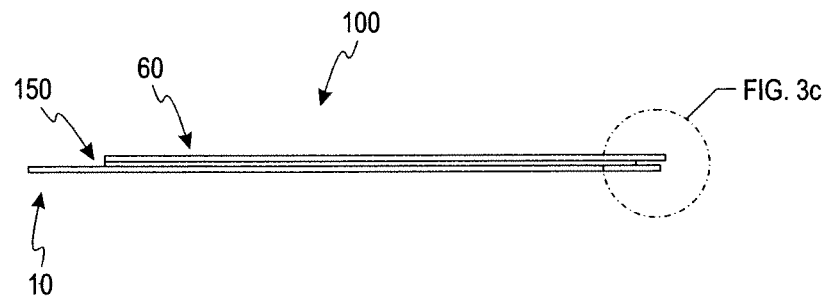
Figure 3C:
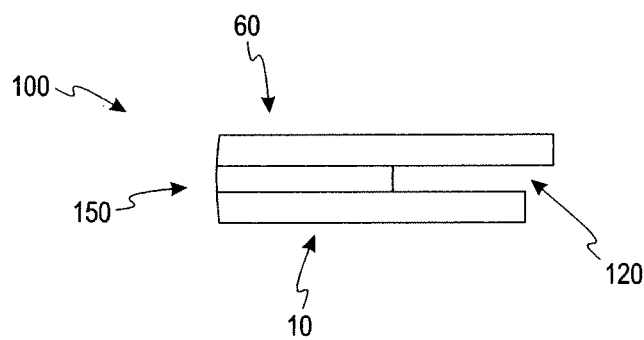
FIG. 3c is an enlarged view of generally circular region FIG. 3c in FIG. 3b.

One non-limiting example of an electrochemical test sensor (electrochemical test sensor 100) is shown in FIGS. 3a, 3b. The test sensor 100 of FIGS. 3a, 3b is formed using a base 10 of FIG. 1 and a lid 60 of FIG. 2. The test sensor 100 of FIGS. 3a, 3b includes the base 10, the lid 60 and an adhesive 150. When the base 10 and the lid 60 are attached together, a fluid chamber 120 (FIG. 3c) is formed. To enhance the sample harvesting, a lower surface of the lid may be treated with surfactant. The fluid chamber 120 provides a flow path for introducing the sample into the test sensor 100 and eventually contacting the electrodes, as will be discussed below. The fluid chamber may be accessible to receiving the fluid sample via one end or a combination of at least one side and one end.

Referring back to FIG. 1, the base 10 is shown that includes a first working electrode 22, a second working electrode 24, a counter electrode 26 and a fluid-receiving area 28. The flow of electrons created by the enzymatic reaction flows through the working electrodes to a meter that measures the magnitude of the current flow. The counter electrode provides a fixed potential against which the working electrodes is controlled. The counter electrode may also be used to complete the electrical circuit. The electrochemical test sensor may also contain additional electrodes. It is contemplated that other electrodes may be used such as a hematocrit electrode that assists in correcting for the bias that occurs with selected hematocrit concentrations or an electrode that detects an underfill condition.

The general operation of the components of an electrochemical test sensor, including their operation, may be found in, for example, U.S. Pat. No. 6,531,040 assigned to Bayer Corporation. It is contemplated that other electrochemical test sensors may be employed.

Electrochemical test sensors of the type known as biosensors include a biochemical recognition element as a sensor reagent. The reagent generally comprises active ingredients and non-reactive or support ingredients. One active ingredient that is included in the electrochemical test sensors of the present invention in one embodiment is glucose oxidase, which assists in determining the glucose measurement of the tested fluid.

Another active ingredient that is included in the electrochemical test sensor of the present invention is a mediator to transfer electrons. The mediator may be an inorganic mediator. Non-limiting examples of mediators that may be included in the test sensors include, ferricyanide derivatives, ruthenium (III) derivatives, and ferricium derivatives. One non-limiting example of a ferricyanide derivative is potassium ferricyanide. It is contemplated that organic mediators (without metal) may also be used. It is contemplated that other mediators in this embodiment may be used as long as the oxidized form of the mediators reacts with glucose oxidase (GO) and the reduced form reacts with peroxidase.

It is contemplated that other ingredients may be added to the sensor reagent. For example, non-reactive ingredients such as stabilizing agents may be added to the sensor reagent to promote a longer shelf life. Other non-reactive ingredients that may be used include, but are not limited to, polymers, binders and surfactants.

The first working electrode 22 includes glucose oxidase, a mediator and peroxidase. In another embodiment, the first working electrode may further include non-reactive ingredients such as discussed above. The peroxidase to be used in the first working electrode may be obtained from a variety of sources. One source for the peroxidase to be used in the first working electrode may be soybean (soybean peroxidase). Another source of the peroxidase that may be used in the first working electrode is horseradish (horseradish root peroxidase). It is contemplated that other sources of peroxidase may be used. The glucose oxidase, mediator, peroxidase and non-reactive ingredients, if any, may be applied to the first working electrode by a coating technique. It is contemplated that these materials may be applied to the first working electrode by other methods such as screen-printing.

The second working electrode 24 includes glucose oxidase and a mediator. To receive the full benefit of correcting the oxygen effect in the test sensor, the second working electrode, desirably does not includes any peroxidase. In another embodiment, the second working electrode may further include non-reactive ingredients such as discussed above.

The electrodes may be formed on the base by a variety of methods such as, for example, printing onto the base. The electrodes are formed of conductive materials such as, for example, metallic materials (e.g., gold, platinum, palladium, rhodium, ruthenium, or combinations thereof) or carbon.

The electrodes may be defined by a laser using a mask. For example, the plurality of electrodes 22, 24, 26 may be defined by using a mask and a laser such as, for example, an Excimer laser or a carbon dioxide-based laser. One example of a mask is a chrome-on-glass mask in which the beam of light is only allowed to pass through selected areas. According to another method, the plurality of electrodes may be defined with a laser using direct writing of the lines. In this method, the laser beam of light is moved so as to define the plurality of electrodes. Lasers that produce a beam of energy capable of removing a layer and that can be moved to form a pattern may be used in this method. Non-limiting examples of such lasers are carbon dioxide-based lasers and yttrium-based lasers such as yttrium aluminum garnet (YAG) lasers.

It is contemplated that the plurality of electrodes may be defined by other methods such as, for example, printing (e.g., screen-printing), coating (e.g., reverse roll), vapor deposition, sputtering, and electrochemical deposition.

To form the test sensor 100 of FIGS. 3a, 3b, the base 10 and the lid 60 are attached. In one embodiment, the base 10 is laminated to the lid 60 via the adhesive 150 to form the test sensor such as shown in FIG. 3b. It is contemplated that other materials may be used that have sticking properties such that the lid and the base remain attached.

The base 10 may be laminated to the lid 60 using, for example, a pressure-sensitive adhesive and/or a hot melt adhesive. Thus, the lamination between the base and the lid uses pressure, heat or a combination thereof. It is contemplated that other materials may be used to attach the base to the second surface. It is contemplated that the base and the lid may be heat-sealed to each other to form the test sensor. This may be accomplished using, for example, sonic welding.

Figure 4A:
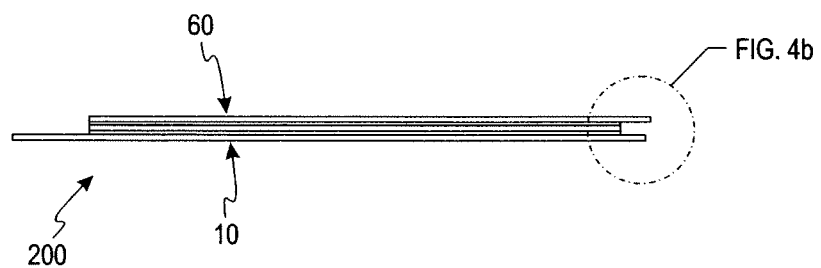
FIG. 4a is a side view of the test sensor using the base of FIG. 1, the lid of FIG. 2 and a spacer according to one embodiment.
Figure 4B:
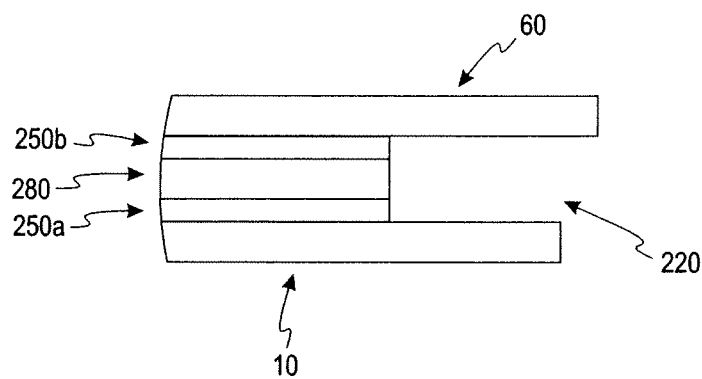

In addition to the embodiment described above in FIGS. 1-3, other electrochemical test sensors may be used in the present invention. Another example of an electrochemical test sensor (test sensor 200) is shown in FIGS. 4a, 4b. The test sensor 200 of FIGS. 4a, 4b may be formed by using the base 10 of FIG. 1, the lid 60 of FIG. 2, and a spacer 280. The test sensor 200 of FIGS. 4a, 4b includes the base 10, the lid 60, the spacer 280 and a fluid chamber 220 is formed when the base, spacer and the lid are attached together. The fluid chamber may be accessible to receiving the fluid sample via one end or a combination of at least one side and an end.

To form the test sensor 200 of FIGS. 4a, 4b, the base 10, the spacer 280, and the lid 60 are attached. In one embodiment, the base 10 and the spacer 280 are attached via an adhesive 250a and the spacer 280 and the lid 60 are attached via an adhesive 250b. The base 10 may be laminated to the spacer 280 using, for example, a pressure-sensitive adhesive and/or a hot melt adhesive. Thus, the lamination between the base and the spacer uses pressure, heat or a combination thereof. It is contemplated that other materials may be used to attach the base to the spacer. Similarly, the lid 60 and the spacer 280 may be attached using the same or a different adhesive than the adhesive used between the base 10 and the spacer 280.

It is contemplated that the lid and spacer may be attached by other methods such as heat sealing. Similarly, the base and the spacer may be attached by other methods such as heat sealing. Thus, in this embodiment, the test sensor would include a base, a spacer and a lid without an adhesive layer. The heat sealing may be accomplished by, for example, sonic welding. For example, the spacer may be made of a lower melting temperature material than the lid and the base.

In another embodiment, the lid or base may be heat-sealed to the spacer with the remaining one of the lid and base being adhesively attached to the spacer. For example, the lid and spacer may be heated sealed and the base is attached to the spacer via an adhesive layer. This would be the same as shown in FIGS. 4a, 4b with the adhesive layer 250b being removed.

According to another embodiment, a spacer-lid combination is used in which the spacer and lid have been previously attached before being attached to the base. According to a further embodiment, a spacer-base combination is used in which the spacer and the base have been previously attached being attached to the lid.

To illustrate the correction of the oxygen effect in one embodiment of the present invention, reactions are shown using, for example, a test sensor with glucose oxidase (GO) and a mediator such as ferricyanide. In this embodiment, the first working electrode includes GO, ferricyanide and peroxidase, while the second working electrode includes GO and ferricyanide. As discussed above, it is contemplated that other mediators may be used.

a. glucose+GO (ox)→gluconic acid+GO (red)  (Equation 1)

b. ferricyanide+GO (red)→ferrocyanide+GO (ox)  (Equation 2)

c. $O_2$+GO (red)→$H_2O_2$+GO (ox)  (Equation 3)

d. peroxidase (red)+$H_2O_2$→peroxidase (ox)+$H_2O$  (Equation 4)

e. peroxidase (ox)+ferrocyanide→peroxidase (red)+ferricyanide  (Equation 5)

Equations 1-3 show the reactions that occur in a test sensor containing glucose oxidase (GO) and ferricyanide. In Equation 1, glucose is converted to gluconic acid by the glucose oxidase. The reduced glucose oxidase converts the ferricyanide to ferrocyanide as shown in Equation 2. During this conversion, the glucose oxidase is oxidized to its original state. The amount of ferrocyanide generated is directly proportional to the glucose concentration in the fluid sample.

The reaction in Equation 3 is undesirable since oxygen competes with ferricyanide in reacting with the glucose oxidase (reduced form). Thus, Equation 3 leads to less ferrocyanide formation and, therefore, a low glucose reading.

To correct for this oxygen effect, peroxidase is added to one of the working electrodes (first working electrode). Equations 4 and 5 show how the peroxidase works. In Equation 4, $H_2O_2$ reacts with peroxidase (reduced form) to form $H_2O$ and peroxidase (oxidized form). The ferrocyanide generated from Equations 1 and 2 then reacts with the peroxidase (oxidized form) to form ferricyanide as shown in Equation 5. The amount of ferrocyanide consumed by the peroxidase is proportional to the amount of $H_2O_2$ and therefore the amount of $O_2$.

The present invention uses a test sensor having at least two working electrodes and one counter electrode. In this embodiment, the first working electrode includes glucose oxidase, ferricyanide and peroxidase, while the second working electrode includes glucose oxidase and ferricyanide. The reactions in Equations 1-5 are present in the first working electrode and reactions in Equations 1-3 are present in the second working electrode.

The corrected measured current is shown in Equation 6:

$$2i-i'=\text{corrected measured current} \quad \text{(Equation 6)}$$

wherein i=the measured current from the second working electrode (without peroxidase); and i'=the measured current from the first working electrode (with peroxidase).

Thus, the oxygen effect is corrected by measuring the current from the first and second working electrodes. In this method, the second working electrode measures a current (i) that is lower than expected because of the oxygen effect. The first working electrode measures a current (i') that is even lower because of the addition reactions that occur in Equations 4 and 5. By subtracting i–i', a correction factor for the oxygen effect is obtained. This number (i–i') is added to the measured current (i) from the second working electrode to calculate the glucose concentration.

A sensor-dispensing instrument, or meter, in one embodiment uses a test sensor adapted to receive a fluid sample to be analyzed. FIG. 5 depicts one non-limiting example of a meter (meter 300). An electrochemical test sensor contacts the meter 300 such that an electronic connection is established. The meter 300 also contains a processor (not shown) adapted to perform a predefined test sequence for measuring a predefined parameter value. The processor is encoded with calibration information, codes, and/or test sequences assigned for use in the clinical value computations corresponding to each test sensor version. A memory is coupled to the processor for storing predefined parameter data values.

A plurality of electrochemical test sensors is typically stored in a disposable cartridge. For example, the plurality of test sensors may be stored in a test-sensor pack where the test sensors are individually packaged in sensor cavities (i.e., a blister-type pack). An example of a disposable cartridge 330 being placed in the meter 300 is depicted in FIG. 5. The disposable cartridge 330 is an example of a blister-type pack. The cartridge 330 includes a plurality of electrochemical test sensors 332 that is individually stored in a respective one of a plurality of sensor cavities 334. The cartridge 330 is generally circular in shape with the sensor cavities 334 extending from near the outer peripheral edge toward and spaced apart from the center of the cartridge 330. It is contemplated, however, that other sensor packs may be of different shapes than that depicted in FIG. 5. For example, the sensor package may be a square, a rectangle, another polygonal shape, or a non-polygonal shape, including oval. The disposable cartridge 330 of FIG. 5 is further described at U.S. Publication No. 2003/0032190 that published on Feb. 13, 2003, and is entitled "Mechanical Mechanism for a Blood Glucose Sensor-Dispensing Instrument." In this embodiment, each sensor cavity 334 accommodates one of the plurality of test sensors 332.

Figure 6A:
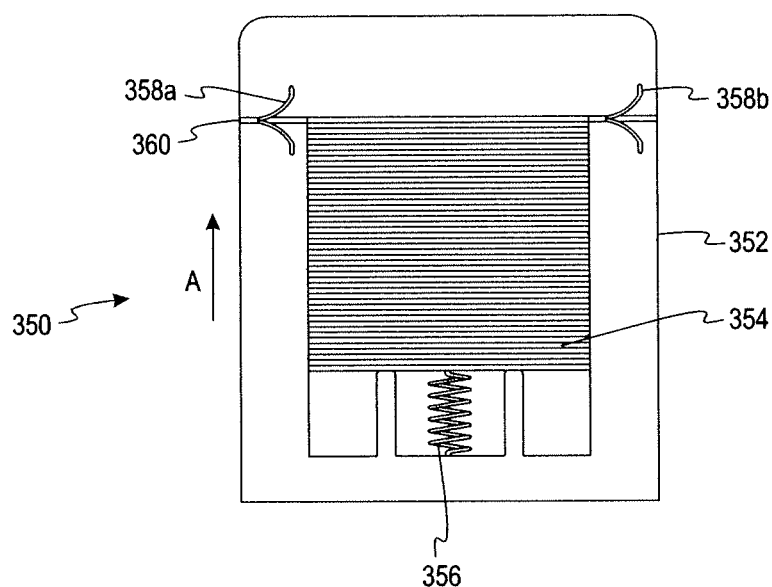
FIG. 6a is a front view of a disposable cartridge with a plurality of stacked test sensors according to one embodiment.
Figure 6B:
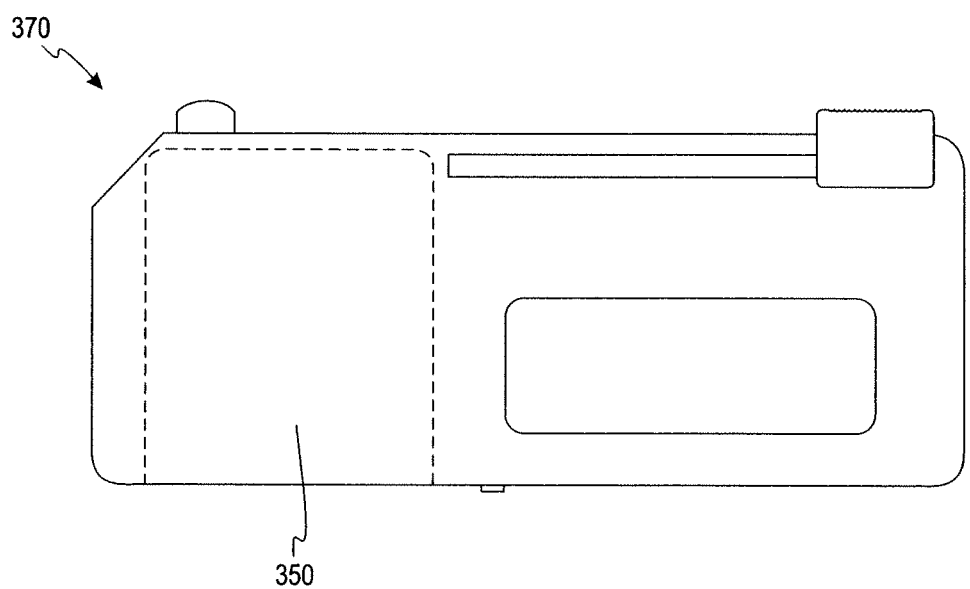

The plurality of test sensors may be stacked in a disposable cartridge such as shown in FIG. 6a. Referring to FIG. 6a, a disposable cartridge 350 includes a housing 352 and a plurality of stacked electrochemical test sensors 354 that is moved in the direction of arrow A via a spring 356. The cartridge 350 also includes a plurality of seals 358a,b that protects the stacked test sensors 354 from humidity. The test sensors 354, one at a time, exit the cartridge 350, via an opening 360. The disposable cartridge 350 may be stored in an instrument or meter 370 of FIG. 6b. It is contemplated that the electrochemical test sensors may be used with other instruments or meters than instruments 300 and 370 depicted in FIGS. 5, 6b. The electrochemical test sensors may also be used in other types of sensor packs than sensor package 332. For example, the electrochemical test sensors may be used in sensor packages such as a drum-type sensor package.

Because of the limited shelf life of many test sensors, the cartridges 330, 350 of FIGS. 5, 6a may vary in the number of electrochemical test sensors that are included so as to address the needs of different users. Typically, the cartridges contain from about 10 to about 100 test sensors and, more specifically, contain from about 25 to about 50 test sensors.

According to other embodiments, other reagents may be used to correct for the oxygen effect. In one embodiment, the reagent cholesterol oxidase is used to reduce the oxygen effect. To illustrate the correction of the oxygen effect in this embodiment, reactions are shown using, for example, a test sensor with cholesterol oxidase and a mediator such as ferricyanide or ferricyanide ion. In this embodiment, the first working electrode includes cholesterol oxidase, ferricyanide and peroxidase, while the second working electrode includes cholesterol oxidase and ferricyanide. It is contemplated that other mediators may be used with the reagent cholesterol oxidase.

a. cholesterol+cholesterol oxidase (ox)→cholesten-3-one+cholesterol oxidase (red) (Equation 7)

b. mediator (ox)+cholesterol oxidase (red)→mediator (red)+cholesterol oxidase (ox) (Equation 8)

c. $O_2$+cholesterol oxidase (red)→$H_2O_2$+cholesterol oxidase (ox) (Equation 9)

d. peroxidase (red)+$H_2O_2$→peroxidase (ox)+$H_2O$ (Equation 10)

e. peroxidase (ox)+mediator (red)→peroxidase (red)+mediator (ox) (Equation 11)

Equations 7-9 show the reactions that occur in a test sensor containing cholesterol oxidase and a mediator such as ferricyanide. In Equation 7, cholesterol is converted to cholesten-3-one by the cholesterol oxidase. The reduced cholesterol oxidase converts the mediator (oxidized) (e.g., ferricyanide) to the mediator (reduced) (e.g., ferrocyanide) as shown in Equation 8. During this conversion, the cholesterol oxidase is oxidized to its original state. The amount of ferrocyanide generated is directly proportional to the cholesterol concentration in the fluid sample.

The reaction in Equation 9 is undesirable since oxygen competes with the mediator ferricyanide in reacting with the cholesterol oxidase (reduced form). Thus, Equation 9 leads to less ferrocyanide formation and, therefore, a low cholesterol reading.

To correct for this oxygen effect, peroxidase is added to one of the working electrodes (first working electrode). Equations 10 and 11 show how the peroxidase works. In Equation 10, $H_2O_2$ reacts with peroxidase (reduced form) to form $H_2O$ and peroxidase (oxidized form). The ferrocyanide generated from Equations 7 and 8 then reacts with the peroxidase (oxidized form) to form ferricyanide as shown in Equation 11. The amount of ferrocyanide consumed by the peroxidase is proportional to the amount of $H_2O$ and therefore the amount of $O_2$.

In this embodiment, the first working electrode includes cholesterol oxidase, a mediator (e.g., ferricyanide) and peroxidase, while the second working electrode includes cholesterol oxidase and ferricyanide. The reactions in Equations 7-11 are present in the first working electrode and reactions in Equations 7-9 are present in the second working electrode.

The corrected measured current is shown in Equation 12:

$2i-i'$=corrected measured current (Equation 12)

wherein i=the measured current from the second working electrode (without peroxidase); and i'=the measured current from the first working electrode (with peroxidase).

Thus, the oxygen effect is corrected by measuring the current from the first and second working electrodes. In this method, the second working electrode measures a current (i) that is lower than expected because of the oxygen effect. The first working electrode measures a current (i') that is even lower because of the addition reactions that occur in Equations 10 and 11. By subtracting i–i', a correction factor for the oxygen effect is obtained. This number (i–i') is added to the measured current (i) from the second working electrode to calculate the cholesterol concentration.

In another embodiment, the reagent lactate oxidase is used to reduce the oxygen effect. To illustrate the correction of the oxygen effect in this embodiment, reactions are shown using, for example, a test sensor with lactate oxidase and a mediator such as ferricyanide or ferrocium ion. In this embodiment, the first working electrode includes lactate oxidase, ferricyanide and peroxidase, while the second working electrode includes lactate oxidase and ferricyanide. It is contemplated that other mediators may be used with the reagent lactate oxidase.

a. L-lactate+lactate oxidase (ox)→pyruvate+lactate oxidase (red) (Equation 13)

b. mediator (ox)+lactate oxidase (red)→mediator (red)+lactate oxidase (ox) (Equation 14)

c. $O_2$+lactate oxidase (red)→$H_2O_2$+lactate oxidase (ox) (Equation 15)

d. peroxidase (red)+$H_2O_2$→peroxidase (ox)+$H_2O$ (Equation 16)

e. peroxidase (ox)+mediator (red)→peroxidase (red)+mediator (ox) (Equation 17)

Equations 13-15 show the reactions that occur in a test sensor containing lactate oxidase and a mediator such as ferricyanide. In Equation 13, lactate is converted to pyruvate by the lactate oxidase. The reduced lactate oxidase converts the mediator (oxidized) (e.g., ferricyanide) to the mediator (reduced) (e.g., ferrocyanide) as shown in Equation 14. During this conversion, the lactate oxidase is oxidized to its original state. The amount of ferrocyanide generated is directly proportional to the lactate concentration in the fluid sample.

The reaction in Equation 15 is undesirable since oxygen competes with the mediator ferricyanide in reacting with the lactate oxidase (reduced form). Thus, Equation 15 leads to less ferrocyanide formation and, therefore, a low lactate reading.

To correct for this oxygen effect, peroxidase is added to one of the working electrodes (first working electrode). Equations 16 and 17 show how the peroxidase works. In Equation 16, $H_2O_2$ reacts with peroxidase (reduced form) to form $H_2O$ and peroxidase (oxidized form). The ferrocyanide generated from Equations 13 and 14 then reacts with the peroxidase (oxidized form) to form ferricyanide as shown in Equation 17. The amount of ferrocyanide consumed by the peroxidase is proportional to the amount of $H_2O_2$ and therefore the amount of $O_2$.

In this embodiment, the first working electrode includes lactate oxidase, a mediator (e.g., ferricyanide) and peroxidase, while the second working electrode includes lactate oxidase and ferricyanide. The reactions in Equations 13-17 are present in the first working electrode and reactions in Equations 13-15 are present in the second working electrode.

The corrected measured current is shown in Equation 18:

$2i-i'$=corrected measured current (Equation 18)

wherein i=the measured current from the second working electrode (without peroxidase); and i'=the measured current from the first working electrode (with peroxidase).

Thus, the oxygen effect is corrected by measuring the current from the first and second working electrodes. In this method, the second working electrode measures a current (i) that is lower than expected because of the oxygen effect. The first working electrode measures a current (i') that is even lower because of the addition reactions that occur in Equations 16 and 17. By subtracting i–i', a correction factor for the oxygen effect is obtained. This number (i–i') is added to the measured current (i) from the second working electrode to calculate the lactate concentration.

In another embodiment, the reagent pyruvate oxidase is used to reduce the oxygen effect. To illustrate the correction of the oxygen effect in this embodiment, reactions are shown using, for example, a test sensor with pyruvate oxidase and a mediator such as ferricyanide or ferrocium ion. In this embodiment, the first working electrode includes pyruvate oxidase, ferricyanide and peroxidase, while the second working electrode includes pyruvate oxidase and ferricyanide. It is contemplated that other mediators may be used with the reagent pyruvate oxidase.

a. pyruvate+phosphate+pyruvate oxidase (ox)
→acetyl phosphate+$CO_2$+pyruvate oxidase (red) (Equation 19)

b. mediator (ox)+pyruvate oxidase (red)→mediator (red)+pyruvate oxidase (ox) (Equation 20)

c. $O_2$+pyruvate oxidase (red)→$H_2O_2$+pyruvate oxidase (ox) (Equation 21)

d. peroxidase (red)+$H_2O_2$→peroxidase (ox)+$H_2O$ (Equation 22)

e. peroxidase (ox)+mediator (red)→peroxidase (red)+mediator (ox) (Equation 23)

Equations 19-21 show the reactions that occur in a test sensor containing pyruvate oxidase and a mediator such as ferricyanide. In Equation 19, pyruvate is converted to acetyl phosphate by the pyruvate oxidase. The reduced pyruvate oxidase converts the mediator (oxidized) (e.g., ferricyanide) to the mediator (reduced) (e.g., ferrocyanide) as shown in Equation 20. During this conversion, the pyruvate oxidase is oxidized to its original state. The amount of ferrocyanide generated is directly proportional to the pyruvate concentration in the fluid sample.

The reaction in Equation 21 is undesirable since oxygen competes with ferricyanide in reacting with the pyruvate oxidase (reduced form). Thus, Equation 21 leads to less ferrocyanide formation and, therefore, a low pyruvate reading.

To correct for this oxygen effect, peroxidase is added to one of the working electrodes (first working electrode). Equations 22 and 23 show how the peroxidase works. In Equation 22, $H_2O_2$ reacts with peroxidase (reduced form) to form $H_2O$ and peroxidase (oxidized form). The ferrocyanide generated from Equations 19 and 20 then reacts with the peroxidase (oxidized form) to form ferricyanide as shown in Equation 23. The amount of ferrocyanide consumed by the peroxidase is proportional to the amount of $H_2O_2$ and therefore the amount of $O_2$.

In this embodiment, the first working electrode includes pyruvate oxidase, ferricyanide and peroxidase, while the second working electrode includes pyruvate oxidase and ferricyanide. The reactions in Equations 19-23 are present in the first working electrode and reactions in Equations 19-21 are present in the second working electrode.

The corrected measured current is shown in Equation 24:

$2i-i'$=corrected measured current (Equation 24)

wherein i=the measured current from the second working electrode (without peroxidase); and i'=the measured current from the first working electrode (with peroxidase).

In this method, the second working electrode measures a current (i) that is lower than expected because of the oxygen effect. The first working electrode measures a current (i') that is even lower because of the addition reactions that occur in Equations 22 and 23. By subtracting i–i', a correction factor for the oxygen effect is obtained. This number (i–i') is added to the measured current (i) from the second working electrode to calculate the pyruvate concentration.

In another embodiment, the reagent xanthine oxidase is used to reduce the oxygen effect. To illustrate the correction of the oxygen effect in the present invention, reactions are shown using, for example, a test sensor with xanthine oxidase and a mediator such as ferricyanide or ferrocium ion. In this embodiment, the first working electrode includes xanthine oxidase, ferricyanide and peroxidase, while the second working electrode includes xanthine oxidase and ferricyanide. It is contemplated that other mediators may be used with the reagent xanthine oxidase.

a. hypoxanthine+$H_2O$+xanthine oxidase (ox)→uric acid+xanthine oxidase (red) (Equation 25)

b. mediator (ox)+xanthine oxidase (red)→mediator (red)+xanthine oxidase (ox) (Equation 26)

c. $O_2$+xanthine oxidase (red)→$H_2O_2$+xanthine oxidase (ox)  (Equation 27)

d. peroxidase (red)+$H_2O_2$→peroxidase (ox)+$H_2O$  (Equation 28)

e. peroxidase (ox)+mediator (red)→peroxidase (red)+mediator (ox)  (Equation 29)

Equations 25-27 show the reactions that occur in a test sensor containing xanthine oxidase and a mediator such as ferricyanide. In Equation 25, xanthine is converted to uric acid by the xanthine oxidase. The reduced xanthine oxidase converts the mediator (oxidized) (e.g., ferricyanide) to the mediator (reduced) (e.g., ferrocyanide) as shown in Equation 26. During this conversion, the xanthine oxidase is oxidized to its original state. The amount of ferrocyanide generated is directly proportional to the xanthine concentration in the fluid sample.

The reaction in Equation 27 is undesirable since oxygen competes with ferricyanide in reacting with the xanthine oxidase (reduced form). Thus, Equation 27 leads to less ferrocyanide formation and, therefore, a low xanthine reading.

To correct for this oxygen effect, peroxidase is added to one of the working electrodes (first working electrode). Equations 28 and 29 show how the peroxidase works. In Equation 28, $H_2O_2$ reacts with peroxidase (reduced form) to form $H_2O$ and peroxidase (oxidized form). The ferrocyanide generated from Equations 25 and 26 then reacts with the peroxidase (oxidized form) to form ferricyanide as shown in Equation 29. The amount of ferrocyanide consumed by the peroxidase is proportional to the amount of $H_2O_2$ and therefore the amount of $O_2$.

In this embodiment, the first working electrode includes xanthine oxidase, ferricyanide and peroxidase, while the second working electrode includes xanthine oxidase and ferricyanide. The reactions in Equations 25-29 are present in the first working electrode and reactions in Equations 25-27 are present in the second working electrode.

The corrected measured current is shown in Equation 30:

$$2i - i' = \text{corrected measured current} \quad \text{(Equation 30)}$$

wherein i=the measured current from the second working electrode (without peroxidase); and
i'=the measured current from the first working electrode (with peroxidase).

Thus, the oxygen effect is corrected by measuring the current from the first and second working electrodes. In this method, the second working electrode measures a current (i) that is lower than expected because of the oxygen effect. The first working electrode measures a current (i') that is even lower because of the addition reactions that occur in Equations 28 and 29. By subtracting i–i', a correction factor for the oxygen effect is obtained. This number (i–i') is added to the measured current (i) from the second working electrode to calculate the xanthine concentration.

Alternate Embodiment A

An electrochemical test sensor adapted to measure glucose and correct for the oxygen effect in a fluid sample, the test sensor comprising:
  a base;
  a first working electrode including glucose oxidase, a mediator and peroxidase;
  a second working electrode including glucose oxidase and the mediator; and a
  a counter electrode,
  wherein the first working electrode, the second working electrode and the counter electrode are located on the base.

Alternate Embodiment B

The test sensor of Alternative Embodiment A wherein the mediator is a ferricyanide derivative.

Alternate Embodiment C

The test sensor of Alternative Embodiment B wherein the ferricyanide derivative is potassium ferricyanide.

Alternate Embodiment D

The test sensor of Alternative Embodiment A wherein the mediator is a ruthenium (III) derivative or a ferricium derivative.

Alternate Embodiment E

The test sensor of Alternative Embodiment A wherein the mediator is an inorganic mediator.

Alternate Embodiment F

An electrochemical test sensor adapted to measure glucose and correct for the oxygen effect in a fluid sample, the test sensor comprising:
  a base;
  a first working electrode including glucose oxidase, a mediator and peroxidase;
  a second working electrode including glucose oxidase and the mediator;
  a counter electrode; and a
  a lid being attached to the base,
  wherein the first working electrode, the second working electrode and the counter electrode are located on either the base or the lid.

Alternative Embodiment G

The test sensor of Alternative Embodiment F wherein the mediator is a ferricyanide derivative.

Alternative Embodiment H

The test sensor of Alternative Embodiment G wherein the ferricyanide derivative is potassium ferricyanide.

Alternative Embodiment I

The test sensor of Alternative Embodiment F wherein the mediator is a ruthenium (III) derivative or a ferricium derivative.

Alternative Embodiment J

The test sensor of Alternative Embodiment F wherein the mediator is an inorganic mediator.

Alternative Embodiment K

The test sensor of Alternative Embodiment F wherein the lid and the base are attached via an adhesive.

Alternative Embodiment L

An electrochemical test sensor adapted to measure glucose and correct for the oxygen effect in a fluid sample, the test sensor comprising:
- a base;
- a first working electrode including glucose oxidase, a mediator and peroxidase;
- a second working electrode including glucose oxidase and the mediator;
- a counter electrode;
- a lid; and
- a spacer being located between the lid and the base, wherein the first working electrode, the second working electrode and the counter electrode are located adjacent to the base.

Alternative Embodiment M

The test sensor of Alternative Embodiment L wherein the mediator is a ferricyanide derivative.

Alternative Embodiment N

The test sensor of Alternative Embodiment L wherein the mediator is a ruthenium (III) derivative or a ferricium derivative.

Alternative Embodiment O

The test sensor of Alternative Embodiment L wherein the mediator is an inorganic mediator.

Alternative Process P

A method for correcting the oxygen effect in determining the concentration of glucose using an electrochemical test sensor, the method comprising the acts of:
- providing a test sensor, the test sensor comprising a base, first and second working electrodes, and a counter electrode, the first working electrode including glucose oxidase, a mediator and peroxidase, the second working electrode including glucose oxidase and the mediator, the first working electrode, the second working electrode and the counter electrode being adjacent to the base;
- contacting the test sensor to a meter to form an electrical connection;
- placing a fluid on the test sensor;
- measuring a first current from the first working electrode;
- measuring a second current from the second working electrode; and
- determining the concentration of glucose using the first current measurement and the second current measurement.

Alternative Process Q

The method of Alternative Process P wherein the fluid is blood.

Alternative Process R

The method of Alternative Process P wherein the mediator is a ferricyanide derivative.

Alternative Process S

The method of Alternative Process R wherein the ferricyanide derivative is potassium ferricyanide.

Alternative Process T

The method of Alternative Process P wherein the mediator is a ruthenium (III) derivative or a ferricium derivative.

Alternative Process U

The method of Alternative Process P wherein the mediator is an inorganic mediator.

Alternative Process V

The method of Alternative Process P wherein the test sensor further includes a lid, the lid and the base being attached via an adhesive.

Alternative Process W

The method of Alternative Process P wherein the test sensor further includes a lid, the lid and the base being attached via heat-sealing.

Alternative Process X

The method of Alternative Process P wherein the test sensor further includes a lid and a spacer, the spacer being located between the base and the lid.

Alternative Embodiment Y

An electrochemical test sensor adapted to measure cholesterol and correct for the oxygen effect in a fluid sample, the test sensor comprising:
- a base;
- a first working electrode including cholesterol oxidase, a mediator and peroxidase;
- a second working electrode including cholesterol oxidase and the mediator; and a
- a counter electrode,
- wherein the first working electrode, the second working electrode and the counter electrode are located on the base.

Alternative Embodiment Z

The test sensor of Alternative Embodiment Y wherein the mediator is a ferricyanide derivative.

Alternative Embodiment A2

The test sensor of Alternative Embodiment Z wherein the ferricyanide derivative is potassium ferricyanide.

Alternative Embodiment B2

The test sensor of Alternative Embodiment Y wherein the mediator is a ruthenium (III) derivative or a ferricium derivative.

Alternative Embodiment C2

The test sensor of Alternative Embodiment Y wherein the mediator is an inorganic mediator.

Alternative Embodiment D2

An electrochemical test sensor adapted to measure cholesterol and correct for the oxygen effect in a fluid sample, the test sensor comprising:
a base;
a first working electrode including cholesterol oxidase, a mediator and peroxidase;
a second working electrode including cholesterol oxidase and the mediator;
a counter electrode; and a
a lid being attached to the base,
wherein the first working electrode, the second working electrode and the counter electrode are located on either the base or the lid.

Alternative Embodiment E2

The test sensor of Alternative Embodiment D2 wherein the mediator is a ferricyanide derivative.

Alternative Embodiment F2

The test sensor of Alternative Embodiment E2 wherein the ferricyanide derivative is potassium ferricyanide.

Alternative Embodiment G2

The test sensor of Alternative Embodiment D2 wherein the mediator is a ruthenium (III) derivative or a ferricium derivative.

Alternative Embodiment H2

The test sensor of Alternative Embodiment D2 wherein the mediator is an inorganic mediator.

Alternative Embodiment I2

The test sensor of Alternative Embodiment D2 wherein the lid and the base are attached via an adhesive.

Alternative Embodiment J2

An electrochemical test sensor adapted to measure cholesterol and correct for the oxygen effect in a fluid sample, the test sensor comprising:
a base;
a first working electrode including cholesterol oxidase, a mediator and peroxidase;
a second working electrode including cholesterol oxidase and the mediator;
a counter electrode;
a lid; and
a spacer being located between the lid and the base,
wherein the first working electrode, the second working electrode and the counter electrode are located adjacent to the base.

Alternative Embodiment K2

The test sensor of Alternative Embodiment J2 wherein the mediator is a ferricyanide derivative.

Alternative Embodiment L2

The test sensor of Alternative Embodiment J2 wherein the mediator is a ruthenium (III) derivative or a ferricium derivative.

Alternative Embodiment M2

The test sensor of Alternative Embodiment J2 wherein the mediator is an inorganic mediator.

Alternative Process N2

A method for correcting the oxygen effect in determining the concentration of cholesterol using an electrochemical test sensor, the method comprising the acts of:
providing a test sensor, the test sensor comprising a base, first and second working electrodes, and a counter electrode, the first working electrode including cholesterol oxidase, a mediator and peroxidase, the second working electrode including cholesterol oxidase and the mediator, the first working electrode, the second working electrode and the counter electrode being adjacent to the base;
contacting the test sensor to a meter to form an electrical connection;
placing a fluid on the test sensor;
measuring a first current from the first working electrode;
measuring a second current from the second working electrode; and
determining the concentration of cholesterol using the first current measurement and the second current measurement.

Alternative Process O2

The method of Alternative Process N2 wherein the fluid is blood.

Alternative Process P2

The method of Alternative Process N2 wherein the mediator is a ferricyanide derivative.

Alternative Process Q2

The method of Alternative Process P2 wherein the ferricyanide derivative is potassium ferricyanide.

Alternative Process R2

The method of Alternative Process N2 wherein the mediator is a ruthenium (III) derivative or a ferricium derivative.

Alternative Process S2

The method of Alternative Process N2 wherein the mediator is an inorganic mediator.

Alternative Process T2

The method of Alternative Process N2 wherein the test sensor further includes a lid, the lid and the base being attached via an adhesive.

Alternative Process U2

The method of Alternative Process N2 wherein the test sensor further includes a lid, the lid and the base being attached via heat-sealing.

Alternative Process V2

The method of Alternative Process N2 wherein the test sensor further includes a lid and a spacer, the spacer being located between the base and the lid.

Alternative Embodiment W2

An electrochemical test sensor adapted to measure at least one of lactate, pyruvate or xanthine and correct for the oxygen effect in a fluid sample, the test sensor comprising:
a base;
a first working electrode including lactate, pyruvate or xanthine oxidase, a mediator and peroxidase;
a second working electrode including lactate, pyruvate or xanthine oxidase and the mediator; and a
a counter electrode,
wherein the first working electrode, the second working electrode and the counter electrode are located on the base.

Alternative Embodiment X2

The test sensor of Alternative Embodiment W2 wherein the mediator is a ferricyanide derivative.

Alternative Embodiment Y2

The test sensor of Alternative Embodiment X2 wherein the ferricyanide derivative is potassium ferricyanide.

Alternative Embodiment Z2

The test sensor of Alternative Embodiment W2 wherein the mediator is a ruthenium (III) derivative or a ferricium derivative.

Alternative Embodiment A3

The test sensor of Alternative Embodiment W2 wherein the mediator is an inorganic mediator.

Alternative Embodiment B3

An electrochemical test sensor adapted to measure at least one of lactate, pyruvate or xanthine and correct for the oxygen effect in a fluid sample, the test sensor comprising:
a base;
a first working electrode including lactate, pyruvate or xanthine oxidase, a mediator and peroxidase;
a second working electrode including lactate, pyruvate or xanthine oxidase and the mediator;
a counter electrode; and a
a lid being attached to the base,
wherein the first working electrode, the second working electrode and the counter electrode are located on either the base or the lid.

Alternative Embodiment C3

The test sensor of Alternative Embodiment B3 wherein the mediator is a ferricyanide derivative.

Alternative Embodiment D3

The test sensor of Alternative Embodiment C3 wherein the ferricyanide derivative is potassium ferricyanide.

Alternative Embodiment E3

The test sensor of Alternative Embodiment B3 wherein the mediator is a ruthenium (III) derivative or a ferricium derivative.

Alternative Embodiment F3

The test sensor of Alternative Embodiment B3 wherein the mediator is an inorganic mediator.

Alternative Embodiment G3

The test sensor of Alternative Embodiment B3 wherein the lid and the base are attached via an adhesive.

Alternative Embodiment H3

An electrochemical test sensor adapted to measure at least one of lactate, pyruvate or xanthine and correct for the oxygen effect in a fluid sample, the test sensor comprising:
a base;
a first working electrode including lactate, pyruvate or xanthine oxidase, a mediator and peroxidase;
a second working electrode including lactate, pyruvate or xanthine oxidase and the mediator;
a counter electrode;
a lid; and
a spacer being located between the lid and the base,
wherein the first working electrode, the second working electrode and the counter electrode are located adjacent to the base.

Alternative Embodiment I3

The test sensor of Alternative Embodiment H3 wherein the mediator is a ferricyanide derivative.

Alternative Embodiment J3

The test sensor of Alternative Embodiment H3 wherein the mediator is a ruthenium (III) derivative or a ferricium derivative.

Alternative Embodiment K3

The test sensor of Alternative Embodiment H3 wherein the mediator is an inorganic mediator.

Alternative Process L3

A method for correcting the oxygen effect in determining the concentration of at least one of lactate, pyruvate or xanthine using an electrochemical test sensor, the method comprising the acts of:

providing a test sensor, the test sensor comprising a base, first and second working electrodes, and a counter electrode, the first working electrode including lactate, pyruvate or xanthine oxidase, a mediator and peroxidase, the second working electrode including lactate, pyruvate or xanthine oxidase and the mediator, the first working electrode, the second working electrode and the counter electrode being adjacent to the base;

contacting the test sensor to a meter to form an electrical connection;

placing a fluid on the test sensor;

measuring a first current from the first working electrode;

measuring a second current from the second working electrode; and determining the concentration of lactate, pyruvate or xanthine using the first current measurement and the second current measurement.

Alternative Process M3

The method of Alternative Process L3 wherein the fluid is blood.

Alternative Process N3

The method of Alternative Process L3 wherein the mediator is a ferricyanide derivative.

Alternative Process O3

The method of Alternative Process N3 wherein the ferricyanide derivative is potassium ferricyanide.

Alternative Process P3

The method of Alternative Process L3 wherein the mediator is a ruthenium (III) derivative or a ferricium derivative.

Alternative Process Q3

The method of Alternative Process L3 wherein the mediator is an inorganic mediator.

Alternative Process R3

The method of Alternative Process L3 wherein the test sensor further includes a lid, the lid and the base being attached via an adhesive.

Alternative Process S3

The method of Alternative Process L3 wherein the test sensor further includes a lid, the lid and the base being attached via heat-sealing.

Alternative Process T3

The method of Alternative Process L3 wherein the test sensor further includes a lid and a spacer, the spacer being located between the base and the lid.

While the invention is susceptible to various modifications and alternative forms, specific embodiments and methods thereof have been shown by way of example in the drawings and are described in detail herein. It should be understood, however, that it is not intended to limit the invention to the particular forms or methods disclosed, but, to the contrary, the intention is to cover all modifications, equivalents and alternatives falling within the spirit and scope of the invention as defined by the appended claims.

The invention claimed is:

1. A method for correcting the oxygen effect in determining the concentration of glucose in a fluid using an electrochemical test sensor, the method comprising the acts of:

providing a test sensor, the test sensor comprising first and second working electrodes, and a counter electrode, the first working electrode including glucose oxidase, an oxidized form of a mediator and peroxidase, the second working electrode including glucose oxidase and the oxidized form of the mediator;

contacting the fluid with the test sensor;

measuring a first current from the first working electrode from a reduced form of the mediator;

measuring a second current from the second working electrode from the reduced form of the mediator; and determining the concentration of glucose and correcting for the oxygen effect by using the first current measurement and the second current measurement.

2. The method of claim 1, wherein the determination of the glucose concentration includes adding the second current measurement to the oxygen effect.

3. The method of claim 1, wherein the fluid is blood.

4. The method of claim 1, wherein the mediator is a ferricyanide derivative.

5. The method of claim 1, wherein the mediator is a ruthenium (III) derivative or a ferricium derivative.

6. The method of claim 1, wherein the mediator is an inorganic mediator.

7. The method of claim 1, further including contacting the test sensor to a meter to form an electrical connection.

8. The method of claim 1, wherein the oxygen effect is determined by subtracting the first current measurement from the second current measurement.

9. A method for correcting the oxygen effect in determining the concentration of glucose in a fluid using an electrochemical test sensor, the method comprising the acts of:

providing a test sensor, the test sensor comprising first and second working electrodes, and a counter electrode, the first working electrode including glucose oxidase, an oxidized form of mediator and peroxidase, the second working electrode including glucose oxidase and the oxidized form of the mediator in the absence of the peroxidase;

contacting the fluid with the test sensor;

measuring a first current from the first working electrode from a reduced form of the mediator;

measuring a second current from the second working electrode from the reduced form of the mediator; and determining the concentration of glucose and correcting for the oxygen effect by using the first current measurement and the second current measurement.

10. The method of claim 9, wherein the determination of the glucose concentration includes adding the second current measurement to the oxygen effect.

11. The method of claim 9, wherein the fluid is blood.

12. The method of claim 9, wherein the mediator is a ferricyanide derivative.

13. The method of claim 9, wherein the oxygen effect is determined by subtracting the first current measurement from the second current measurement.

14. A method for correcting the oxygen effect in determining the concentration of cholesterol in a fluid using an electrochemical test sensor, the method comprising the acts of:

providing a test sensor, the test sensor comprising first and second working electrodes, and a counter electrode, the first working electrode including cholesterol oxidase, an oxidized form of mediator and peroxidase, the second working electrode including cholesterol oxidase and the oxidized form of the mediator;

contacting the fluid with the test sensor;

measuring a first current from the first working electrode from a reduced form of the mediator;

measuring a second current from the second working electrode from the reduced form of the mediator; and determining the concentration of cholesterol and correcting for the oxygen effect by using the first current measurement and the second current measurement.

15. The method of claim 14, wherein the oxygen effect is determined by subtracting the first current measurement from the second current measurement.

16. The method of claim 14, wherein the determination of the cholesterol concentration includes adding the second current measurement to the oxygen effect.

17. The method of claim 14, wherein the second working electrode including cholesterol oxidase and the mediator is formed in the absence of the peroxidase.

18. A method for correcting the oxygen effect in determining the concentration of at least one of lactate, pyruvate or xanthine in a fluid using an electrochemical test sensor, the method comprising the acts of:

providing a test sensor, the test sensor comprising first and second working electrodes, and a counter electrode, the first working electrode including lactate, pyruvate or xanthine oxidase, an oxidized form of mediator and peroxidase, the second working electrode including lactate, pyruvate or xanthine oxidase and the oxidized form of the mediator;

contacting the fluid with the test sensor;

measuring a first current from the first working electrode from a reduced form of the mediator;

measuring a second current from the second working electrode from the reduced form of the mediator; and determining the concentration of lactate, pyruvate or xanthine and correcting of the oxygen effect by using the first current measurement and the second current measurement.

19. The method of claim 18, wherein the oxygen effect is determined by subtracting the first current measurement from the second current measurement.

20. The method of claim 18, wherein the determination of the lactate, pyruvate or xanthine concentration includes adding the second current measurement to the oxygen effect.

21. The method of claim 14, wherein the second working electrode including lactate, pyruvate or xanthine oxidase and the mediator is formed in the absence of the peroxidase.

* * * * *